(12) United States Patent
Hamada

(10) Patent No.: US 6,326,497 B1
(45) Date of Patent: Dec. 4, 2001

(54) PROCESS FOR PRODUCING AMINOMETHYLATED HETEROCYCLIC DERIVATIVE

(75) Inventor: Yusuke Hamada, Sizuoka-ken (JP)

(73) Assignee: Ihara Chemical Industries Co. Ltd., Tokyo (JP)

( * ) Notice: Subject to any disclaimer, the term of this patent is extended or adjusted under 35 U.S.C. 154(b) by 0 days.

(21) Appl. No.: 09/581,073

(22) PCT Filed: Oct. 12, 1999

(86) PCT No.: PCT/JP99/05621

§ 371 Date: Jun. 9, 2000

§ 102(e) Date: Jun. 9, 2000

(87) PCT Pub. No.: WO00/21943

PCT Pub. Date: Apr. 20, 2000

(30) Foreign Application Priority Data

Oct. 12, 1998 (JP) .................................................. 10-304765

(51) Int. Cl.⁷ .................................................. C07D 277/20
(52) U.S. Cl. .................................................. 548/202
(58) Field of Search ............................................. 548/202

(56) References Cited

U.S. PATENT DOCUMENTS 5,180,833    1/1993   Uneme et al. .
5,756,769    5/1998   Seko et al. .

FOREIGN PATENT DOCUMENTS 4-5262       1/1992   (JP) .
5043504      2/1993   (JP) .
07-188170    7/1995   (JP) .

*Primary Examiner*—Robert Gerstl
(74) *Attorney, Agent, or Firm*—Armstrong, Westerman Hattori, McLeland & Naughton, LLP (57) ABSTRACT

A heterocyclic halide represented by a general formula (I):

$$T-CH_2-Y \qquad (I)$$

(wherein T denotes a heterocyclic group, and Y denotes a chlorine atom, bromine atom or iodine atom), is reacted with ammonia in the presence of an aromatic aldehyde represented by a general formula (II):

$$A-CHO \qquad (II)$$

(wherein A denotes an aromatic group), to thereby produce an aminomethyl-heterocyclic derivative represented by a general formula (III):

$$T-CH_2-N=CH-A \qquad (III)$$

(wherein T denotes a heterocyclic group, and A denotes an aromatic group).

6 Claims, 4 Drawing Sheets

Conc.Level:0    Calc.Method:0(Area%)    PA:1.00000    PB:1.00000

| No. | NAME | RT | AREA | MARK | CONC | HEIGHT |
|---|---|---|---|---|---|---|
| 1 | | 4.405 | 3185850 | | 48.3277 | 405659 |
| 2 | | 5.546 | 62124 | | 0.9423 | 7223 |
| 3 | | 6.005 | 12394 | | 0.1880 | 1055 |
| 4 | | 6.378 | 10994 | | 0.1667 | 929 |
| 5 | | 8.181 | 226130 | | 3.4302 | 23388 |
| 6 | | 10.512 | 2942 | | 0.0446 | 157 |
| 7 | | 13.024 | 3084620 | | 46.7921 | 227304 |
| 8 | | 16.469 | 7122 | | 0.1080 | 400 |
| | TOTAL | | 6592177 | | 100.0000 | 666115 |

Fig.4

| No. | NAME | RT | AREA | MARK | CONC | HEIGHT |
|---|---|---|---|---|---|---|
| 1 | | 4.389 | 85948 | | 0.0238 | 11200 |
| 2 | | 5.568 | 51341 | | 0.0142 | 4155 |
| 3 | | 7.328 | 8743 | | 0.0024 | 796 |
| 4 | | 8.149 | 7101000 | | 1.9691 | 663168 |
| 5 | | 9.269 | 7080 | | 0.0019 | 656 |
| 6 | | 9.738 | 4949 | | 0.0013 | 526 |
| 7 | | 10.154 | 34552 | | 0.0095 | 2090 |
| 8 | | 11.616 | 11048 | | 0.0030 | 502 |
| 9 | | 12.560 | 71449 | M | 0.0198 | 4424 |
| 10 | | 12.976 | 2994180 | | 0.8303 | 207157 |
| 11 | | 14.064 | 872480 | | 0.2419 | 32331 |
| 12 | | 14.864 | 13949 | | 0.0038 | 1095 |
| 13 | | 15.328 | 12755 | | 0.0035 | 964 |
| 14 | | 15.749 | 146142 | | 0.0405 | 9792 |
| 15 | | 16.298 | 62173 | | 0.0172 | 3879 |
| 16 | | 16.874 | 38768 | | 0.0107 | 2491 |
| 17 | | 17.514 | 2037 | | 5.65089E-04 | 145 |
| 18 | | 17.749 | 7127 | | 0.0019 | 477 |
| 19 | | 19.413 | 342877000 | O | 95.0829 | 10154234 |
| 20 | | 25.226 | 2484 | | 6.88924E-04 | 149 |
| 21 | | 26.272 | 88856 | | 0.0246 | 3473 |
| 22 | | 29.696 | 83998 | | 0.0232 | 2467 |
| 23 | | 31.168 | 30036 | | 0.0083 | 1117 |
| 24 | | 36.213 | 735366 | | 0.2039 | 27863 |
| 25 | | 37.408 | 5265050 | | 1.4600 | 151045 |
| | TOTAL | | 360608518 | | 100.0000 | 11286196 |

PROCESS FOR PRODUCING AMINOMETHYLATED HETEROCYCLIC DERIVATIVE

TECHNICAL FIELD

The present invention relates to a process for producing an aminomethyl-heterocyclic derivative which is useful as an intermediate to produce biologically active substances such as medicines and agricultural chemicals, with a good yield, while suppressing the formation of by-products.

BACKGROUND ART

In general, it is known that aminomethyl-heterocyclic derivatives such as aminomethyl-thiazoles are useful as intermediates to produce biologically active substances such as medicines and agricultural chemicals.

With respect to aminomethyl-thiazoles as one kind of such aminomethyl-heterocyclic derivatives, there is known a process for producing aminomethyl-thiazoles by reacting a chloromethyl-thiazole with an excess of aqueous ammonia solution so as to convert the chloro-group of the raw material into an amino group (KOKAI (Unexamined Patent Publication) No. Hei. 4-234864). However, in this process, in addition to the aminomethyl-thiazole as the desired product, there are inevitably produced the dimer and the trimer of the desired product which are attributable to a further reaction of the aminomethyl-thiazole per se with the chloromethyl-thiazole as the raw material. Therefore, this process is not advantageous, in view of the industrial practice thereof as well as in view of the protection of surrounding environment.

There is also known a process wherein halomethyl thiazole is reacted with potassium phthalimide, and the resultant product is further reacted with hydrazine (Published European Patent No. 302389). However, the potassium phthalimide is a relatively expensive reagent and, further, the production of waste at the time of the decomposition of the hydrazine causes an industrially or environmentally serious problem.

Further, there is also known a process wherein halomethyl thiazole is reacted with hexamethylene tetramine, and the resultant product is subsequently subjected to solvolysis by the use of mineral acid (KOKAI No. Hei. 4-234864). However, in this process, only one nitrogen atom among the four nitrogen atoms of the hexamethylene tetramine is consumed by the real reaction, and the remainder of the nitrogen atoms only cause waste. Therefore, this process is not advantageous both in view of industrial practice and in view of the environment.

DISCLOSURE OF INVENTION

An object of the present invention is to provide a production process which is capable of providing an aminomethyl-heterocyclic compound (such as aminomethyl-thiazoles), with a good yield while controlling the formation of by-products.

Another object of the present invention is to provide a production process which is capable of providing an aminomethyl-heterocyclic compound easily and at high purity.

As a result of earnest study, the present inventor has found that the reaction of a specific heterocyclic halide compound with ammonia in the presence of an aromatic aldehyde provides a desired aminated product, with a good yield, while effectively suppressing the formation of by-products such as the dimer and the trimer, although an unreacted halogenated compound is co-present with the free aminated product produced in the same reaction system.

The process for producing an aminomethyl-heterocyclic compound according to the present invention is based on above discovery and, more specifically, it is a process wherein a heterocyclic halide compound represented by a general formula (I):

T—CH$_2$—Y  (I)

(wherein T denotes a heterocyclic group, and Y denotes a chlorine atom, bromine atom or iodine atom), is reacted with ammonia in the presence of an aromatic aldehyde represented by a general formula (II):

A—CHO  (II)

(wherein A denotes an aromatic group), to thereby produce a Schiff base (protected aminated product) represented by a general formula (III):

T—CH$_2$—N=CH—A  (III).

According to the present inventor's knowledge, the reason why the above-mentioned production process according to the present invention can provide a desired Schiff base in good yield while effectively suppressing the formation of by-products such as the dimer and the trimer, although an unreacted halogenated product is co-present with the free aminated product produced in the same reaction system, is presumed to be that the free aminated product which has been produced by the reaction of the heterocyclic halide compound as the raw material with ammonia is rapidly reacted with an aromatic aldehyde to provide the Schiff base in preference to the reaction of the free aminated product with the halide, and therefore the formation of the by-products such as the dimer and the trimer which can be produced by a further reaction of the free aminated compound as the product with the halide as the raw material is effectively prevented, and hence the desired Schiff base is provided in good yield.

BEST MODE FOR CARRYING OUT THE INVENTION

Hereinafter, the present invention will be described, in detail, with reference to the accompanying drawings. In the following description, "%" and "part(s)" representing a quantitative proportion or ratio are those based on weight, unless otherwise noted specifically.
(Heterocyclic Halide Compound)

In the production process according to the present invention, the heterocycle constituting the heterocyclic halide compound (raw material X) is not particularly limited, as long as the raw material reacts with ammonia to provide an aminated product. As such a heterocycle, it is preferred to use those which contain one or more hetero atoms selected from O, S and N, and comprise a three to nine-membered ring, more preferably four to seven-membered ring (particularly five or six-membered ring).

The halogen atom constituting the raw material X is not particularly limited, as long as the raw material X reacts with ammonia to provide an aminated product.

In the present invention, a heterocyclic halide compound represented by the following formula (I):

(I)

(wherein T denotes a heterocyclic group, and Y denotes chlorine atom, bromine atom or iodine atom) may preferably be used. In general, it is considered that a halide compound which is susceptible to hydrolysis is not suitable for the amination thereof with aqueous ammonia, since by-products due to the hydrolysis thereof are inevitably produced. However, in the present invention, it is possible to suitably use such a halide even when it is susceptible to hydrolysis.

More specifically, such a "halide susceptible to hydrolysis" may preferably be one which provides a ratio (b/a) of 1.1 or more, more preferably 1.2 or more (particularly 1.5 or more), provided that a (moles) denotes the number of moles of the OH-product (benzyl alcohol) which has been produced from benzyl chloride, $C_6H_5CH_2Cl$ under the following hydrolysis conditions, and b (moles) denotes the number of moles of the OH-product, T—CH$_2$—OH which has been derived from the heterocyclic halide compound to be used in the present invention under the following hydrolysis conditions.

<Hydrolysis Conditions>
  Halide (benzyl chloride or heterocyclic halide compound): 1 mole
  Ammonia: 6 moles
  Solvent (water): 1000 ml
  Temperature: 70° C.
  Time for hydrolysis: Six hours

<Quantitative Determination of OH-product>

The OH-product can preferably be determined quantitatively by a liquid chromatography (HPLC) under the following conditions. In view of the accuracy and reproducibility of the measured values, the OH-product may preferably be determined quantitatively by an internal standard method using an internal standard substance (e.g., benzoic acid, $C_6H_5$—COOH).

HPLC apparatus: trade name: Module 1 plus, mfd. by Waters Co.
  Column: YMC-A-313 (6.0 mm×250 mm)
  Mobile phase: acetonitrile/0.1% phosphoric acid=3:7
  Flow rate: 1 ml/min.
  Wavelength: 250 nm
  Temperature: 40° C.

As these heterocycles, it is possible to use, e.g., thiazole, imidazole, oxazole, pyrrole, furan, thiophene, pyridine, quinoline, benzimidazole, benzoxazole, benzothiazole, pyrimidine, etc. Such heterocyclic halide compounds can be obtained by ordinary processes (with respect to the details of the process for producing heterocyclic halide compounds, e.g., the reference "Chemistry of Heterocyclic Compounds" (1988), published by KODANSHA may be referred to). Among these, in view of the reactivity of the heterocyclic halide and the usability of the aminated product, it is particularly preferred to use thiazole, oxazole, etc.

In addition, in view of the usability of the product, halomethyl thiazoles represented by the following general formula (IV) may preferably be used in the process according to present invention.

(IV)

(wherein X denotes a halogen atom, and Y denotes chlorine atom, bromine atom or iodine atom.)

In the present invention, for example, the following combinations of X and Y are preferred.

| <X> | <Y> |
|---|---|
| Cl | Cl |
| Cl | Br |
| Cl | I |
| Br | Cl |
| Br | Br |
| Br | I |

More specifically, as the halomethyl thiazoles represented by such general formula (IV), for example, those compounds wherein the substituent Y in the general formula (IV) is a chlorine atom, bromine atom, or iodine atom, and the substituent X is a halogen atom (more specifically, fluorine atom, a chlorine atom, bromine atom, or iodine atom) may preferably be used for the process according to the present invention. Among these, as particularly preferred examples, it is possible to exemplify, e.g., 2-chloro-5-(chloromethyl) thiazole, 2-bromo-5-(chloromethyl)thiazole, 2-bromo-5-(bromomethyl )thiazole, and 2-bromo-4-(chloromethyl) thiazole, but those preferably usable in the present invention are not particularly limited to these specific examples.

These halomethyl thiazoles may be obtained by a process wherein 2,3-dihalo-1-propene which is obtainable by the process as described in KOKAI No. Hei. 7-278027, etc., is converted into 3-isothiocyanato-2-halo-1-propene by the process as described in KOKAI No. Hei. 9-163874, etc., and thereafter this product is halogenated and heat-cyclized by the process as described in KOKAI No. Hei. 4-234864, etc. Further, halomethyl thiazoles are also obtainable by the process as described in KOKAI No. Hei. 9-176140, and the process as described in KOKAI No. Hei. 9-202778.

(Aromatic Aldehyde)

In the present invention, an aromatic aldehyde represented by the following general formula (II):

(II)

(wherein, A denotes aromatic group) may preferably be used. The aromatic group A is not particularly limited, as long as the above aldehyde (II) is rapidly reacted with the free aminated compound as a product (in preference to the reaction thereof with the raw material halide and/or the solvolysis reaction thereof) so as to provide a Schiff base.

In view of ease in availability, an aromatic aldehyde represented by the following general formula (V):

(V)

(wherein, Q denotes a hydrogen atom, a halogen atom or an alkyl group containing 1–5 carbon atoms, and n denotes an integer of 1 or 2) may particularly preferably be used.

For example, in the present invention, the following combinations of Q and n are preferred.

| <Q> | <n> |
|---|---|
| H | 1 |
| Cl | 1 |
| Cl | 2 |
| F | 1 |
| Me | 1 |
| Me | 2 |
| Et | 1 |

As such an aromatic aldehyde, it is preferred to use compounds having a substituent Q in the general formula (V) of a hydrogen atom; halogen atom (fluorine atom, chlorine atom, bromine atom, iodine atom, etc.); an alkyl group containing 1–5 carbon atoms, more specifically, methyl group, ethyl group, n-propyl group, i-propyl group, n-butyl group, i-butyl group, t-butyl group, sec-butyl group, n-pentyl group, i-pentyl group, 2-methylbutyl group, 2,2-dimethylpropyl group, etc.

More specific examples of these preferred aromatic aldehydes may include, e.g., benzaldehyde, 2-chlorobenzaldehyde, 3-chlorobenzaldehyde, 4-chlorobenzaldehyde, 2-fluorobenzaldehyde, 3-fluorobenzaldehyde, 4-fluorobenzaldehyde, 2,4-dichlorobenzaldehyde, 4-methyl benzaldehyde, 4-ethyl benzaldehyde, 2,4-dimethyl benzaldehyde, etc., but the preferred aromatic aldehydes are not limited to these specific examples.

In the present invention, it is preferred to use 1 mole or more, more preferably 1–3 moles of the aromatic aldehyde (II) with respect to 1 mole of the heterocyclic halide compound (I) in the step wherein the heterocyclic halide compound as the raw material is reacted with ammonia in the presence of the aromatic aldehyde (II).

(Ammonia)

It is preferred to use ammonia at a ratio of 2 mole or more, more preferably 2–10 moles, particularly of 2–8 moles (in terms of ammonia) with respect to 1 mole of the heterocyclic halide compound (I) as the raw material.

The ammonia can be added as a gas, but it may preferably be added as an aqueous ammonia solution in view of simple and easy operation and handling. The concentration of the ammonia to be added as an aqueous ammonia solution can generally be in the range of 1–28%. However, the concentration of 5–28% is preferred since the reaction proceeds slowly when the concentration of the ammonia is too low. As the aqueous ammonia solution, for example, a commercially available aqueous ammonia solution (25–28%), etc., can be used as such, in conjunction with an appropriate dilution thereof as desired.

As desired, ammonia gas can be add to the reaction system by an operation such as bubbling at the time of the initiation of or in the course of the reaction. In this case, it is preferred to blow ammonia into the reaction system in an amount (based on the raw material) of 2 moles equivalent or more (more preferably about 2–3 moles equivalent) from a cylinder, etc., over a period of time of about 1–24 hours (more preferably about 5–9 hours). At this time, all of the gas which has been blown into the reaction mixture is not always absorbed by the reaction mixture, and therefore it is preferred to maintain a condition such that a certain amount of off-gas (excess gas) is emitted from the reaction system (i.e., a condition such that the reaction system is substantially saturated with ammonia).

The amination reaction may also be conducted in a closed system as desired. In this case, for example, the pressure in the closed system may preferably be about 0.02–2.0 kg/cm$^2$ (1960–196133 Pa) as determined by a measuring gauge or water column.

(Amination Reaction)

In the present invention, the amination of the halogen group may be conducted in a substantially homogeneous solvent system, or in a two-phase solvent system as desired.

(Solvent)

The solvent to be used is not particularly limited, as long as it does not substantially hinder the above-mentioned amination. A water-type or aqueous solvent may preferably be used in view of the safety, the influence thereof on the surrounding environment, and the reaction rate.

This amination reaction may be conducted by using as a solvent only the water content which has been introduced into the reaction system by the use of an aqueous ammonia solution, but it is also possible to appropriately add thereto another solvent as desired. For example, as the "other solvent", there are exemplified water-soluble solvents including alcohols such as methanol, ethanol, propanol, and isopropanol; and solvents which are substantially water-insoluble and inert to the reaction including: aromatic hydrocarbons represented by benzene, toluene, xylene, chlorobenzene, dichlorobenzene, etc.; and halogenated hydrocarbons represented by chloroform, carbon tetrachloride, etc.

In view of the efficiency of the reaction and the convenience of handling, the amount of the solvent to be used (total amount) may preferably be about 10–3000 ml, more preferably about 100–2000 ml, particularly about 100–1000 ml with respect to 1 mole of the heterocyclic halide compound (I) as the raw material.

(Other Component)

In view of reduction in the reaction time, it is possible to add a quaternary ammonium salt such as tetramethylammonium chloride, tetrabutylammonium chloride, tetrabutylammonium bromide, benzyltriethylammonium chloride, as a catalyst to the reaction system as desired. The addition amount of such a salt may preferably be generally in the range of about 0.01–10 moles %, more preferably in the range of about 0.05–5 moles % with respect to 1 mole of the heterocyclic halide compound (I).

(Reaction Conditions)

The reaction temperature for the amination reaction in the present invention is not particularly limited, but in view of cost, etc., but it may preferably be in the range of from 30° C. to boiling point of the solvent, more preferably in the range of 50–80° C. The reaction time is also dependent on the mole ratio of the raw materials and reaction conditions such as reaction temperature, but it may preferably be in the range of generally 1–24 hours, more preferably in the range of 5–9 hours.

(Schiff Base)

By the amination process according to the present invention, a Schiff base represented by the general formula (III):

$$T—CH_2—N=CH—A \quad (III)$$

as a protected aminated product is provided.

The thus obtained Schiff base can be separated from another reaction product as desired by an ordinary method such as extraction with an organic solvent.

The aromatic aldehyde used for protecting the amino group and Schiff base in the present invention are generally hardly water-soluble, and therefore an organic layer may be separated from the reaction system in some cases when the reaction system is left standing after the completion of the reaction. In this case, the Schiff base may be obtained by separating the organic layer from the reaction system, and further, as desired, extracting the organic layer with an appropriate solvent such as diethyl ether so as to take out the resultant organic layer, and distilling off the extracting solvent as desired.

(Deprotected Aminated Product)

The Schiff base as the above-mentioned Schiff base may be deprotected by an ordinary method. For example, the Schiff base may be deprotected easily and mildly by hydrolyzing the Schiff base with mineral acid.

As the mineral acid which is usable for such hydrolysis treatment, it is possible to exemplify hydrochloric acid, sulfuric acid, phosphoric acid, nitric acid, etc., and commercially available 35% aqueous hydrochloric acid can be used as it is. As the amount of the mineral acid, 1 mole or more, more preferably about 1–2 moles thereof is suitable with respect to 1 mole of the heterocyclic halide compound to be used as the raw material.

The hydrolysis treatment using the mineral acid may preferably be conducted at 10–100° C., more preferably 20° C.–60° C. The time required for the hydrolysis treatment is also dependent on the concentration of the mineral acid to be used and other reaction conditions such as temperature for the hydrolysis treatment, but it may preferably be conducted generally in the range of about 0.5–3 hours.

Further, in this hydrolysis treatment, as desired, it is possible to use a solvent which is substantially water-insoluble and is inert to the hydrolysis reaction, including aromatic hydrocarbons such as benzene, toluene, xylene, chlorobenzene, and dichlorobenzene; and ethers such as diethyl ether.

The reaction mixture is generally separated, into an oily layer and an aqueous layer, when it is left standing after the hydrolysis treatment or when an appropriate organic solvent is added to the reaction mixture after the completion of the hydrolysis and the reaction mixture is stirred, and thereafter it is left standing. The desired deprotected aminated product (VI) may be obtained by taking out the aqueous layer containing the desired mineral acid salt, adjusting this aqueous layer to a pH of about 8–14, preferably a pH of about 9–14 by using alkali, and then conducting ordinary isolation and purification treatment such as extraction and distillation after the above pH adjustment.

As to the alkali to be used for such pH adjustment, it is suitable to use, e.g., hydroxides of alkali metal and alkaline earth metal such as sodium hydroxide, and potassium hydroxide. The alkali may be added by a method such that the alkali per se is added to the aqueous layer which has been taken out so as to dissolve the alkali in the aqueous layer, or the alkali is added to the aqueous layer as an aqueous alkaline solution. As desired, the deprotected aminated product can be taken out as a mineral acid salt or an aqueous solution of the mineral acid salt.

On the other hand, it is possible to recover from the thus remaining oily layer the aromatic aldehyde (II) which has been used in the step of reacting the above-mentioned heterocyclic halide compound (I) with the aqueous ammonia solution. The aromatic aldehyde (II) which has been recovered in this way can again be used for the production process according to the present invention, and therefore such recovery is preferred both in view of the raw material cost and in view of environmental protection.

(Ratio of OH-product/product)

In the present invention, the ratio of (OH-product)/(desired product (VI)) in the deprotected aminated product to be produced after the deprotection treatment may preferably be 50 moles % or below, more preferably 30 moles % or below (particularly 20 moles % or below).

At this time, the OH-product and the desired product (formula (VI)) may preferably be determined quantitatively by HPLC analysis which is similar to that used for the above-mentioned quantitative determination of the OH-product which has been produced by the hydrolysis of the raw material.

(Ratio of Dimer/product)

In the present invention, the ratio of (dimer)/(desired product (VI)) in the deprotected aminated product to be produced after the deprotection treatment may preferably be 5 moles % or below, more preferably 2 moles % or below.

At this time, the dimer and the desired product (formula (VI)) may preferably be determined quantitatively by HPLC analysis which is similar to that used for the above-mentioned quantitative determination of the OH-product which has been produced by the hydrolysis of the raw material.

EXAMPLES

Hereinafter, the present invention is described in further detail with reference to Examples.

Example 1

Into a three-necked flask (internal volume: about 50 ml) equipped with a thermometer and a stirrer, 4.7 g (0.028 mole) of 2-chloro-5-(chloromethyl)thiazole, 20 ml of water, 3.57 g (0.034 mole) of benzaldehyde and 11.4 g (0.17 mole) of a 25% aqueous ammonia solution were added to and the resultant mixture was subjected to reaction under stirring at about 60° C. for nine hours.

The thus obtained reaction mixture was cooled to room temperature and thereafter was extracted with 20 ml of diethyl ether, and the resultant diethyl ether solution was concentrated to about 5 ml by using a rotary evaporator. 5.3 g (0.051 mole) of 35% hydrochloric acid was added dropwise to the resultant concentrated liquid, and thereafter the mixture was stirred at 40° C. for two hours. The reaction mixture was cooled to room temperature, and then 20 ml of ethyl acetate was added thereto and stirred, the resultant mixture was allowed to stand, and the resultant aqueous layer was taken out therefrom. The thus obtained aqueous layer was adjusted to a pH of 11 with a 23% aqueous sodium hydroxide solution and was stirred for 0.5 hour at room temperature. This reaction mixture was extracted with about 50 ml of n-butanol and the extract was washed with water and dried over anhydrous sodium sulfate. The insoluble matter was removed by filtration, and thereafter the filtrate was concentrated under vacuum to thereby provide 3.8 g (yield 91.4%, purity 92%) of crude 5-aminomethyl-2-chlorothiazole. The resultant product was further distilled at 73–75° C./1 mmHg (=133.322 Pa) to thereby obtain 3.4 g (yield 81.5%) of 5-aminomethyl-2-chlorothiazole having a purity of 99.5% or more.

Figure 1:
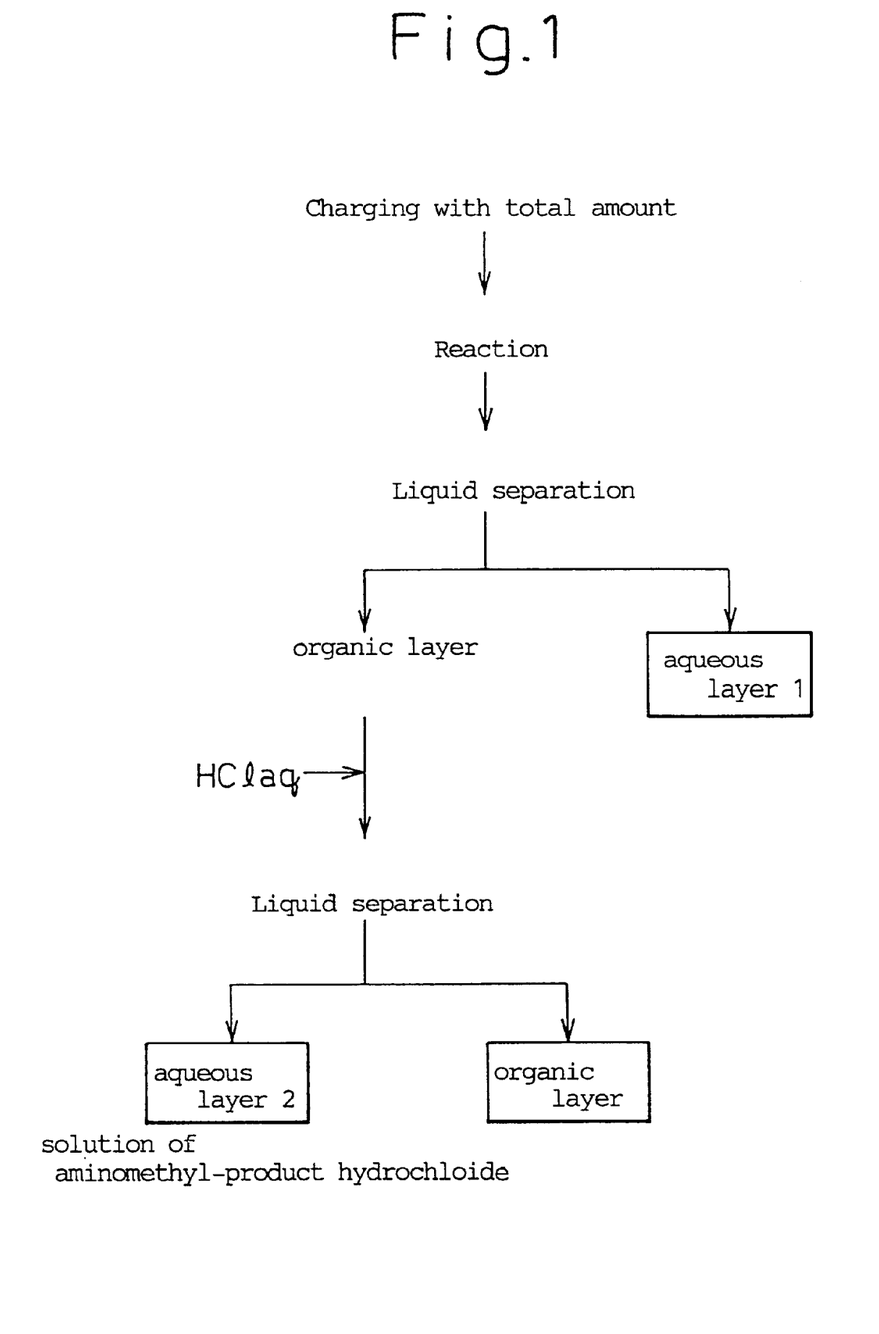
FIG. 1 is a flow chart schematically showing the reaction and liquid-separating procedure used in Examples appearing hereinafter.

FIG. 1 shows the process flow chart used in the above procedure. Each of the "aqueous layer (1)", the "aqueous layer (2)" and the "organic layer" obtained by the above liquid-separating procedure as shown in FIG. 1 was analyzed by HPLC under the following conditions.

HPLC apparatus: trade name: Module-1 plus, mfd. by Waters Co.

Column: YMC-A-313 (6.0 mm×250 mm)

Mobile phase: acetonitrile/0.1%-phosphoric acid=3:7

Flow rate: 1 ml/min.

Wavelength: 250 nm

Temperature: 40° C.

Internal standard substance: benzoic acid

Data processing apparatus: trade name: Chromatocorder 21, mfd. by Sick Co.

Figure 2:
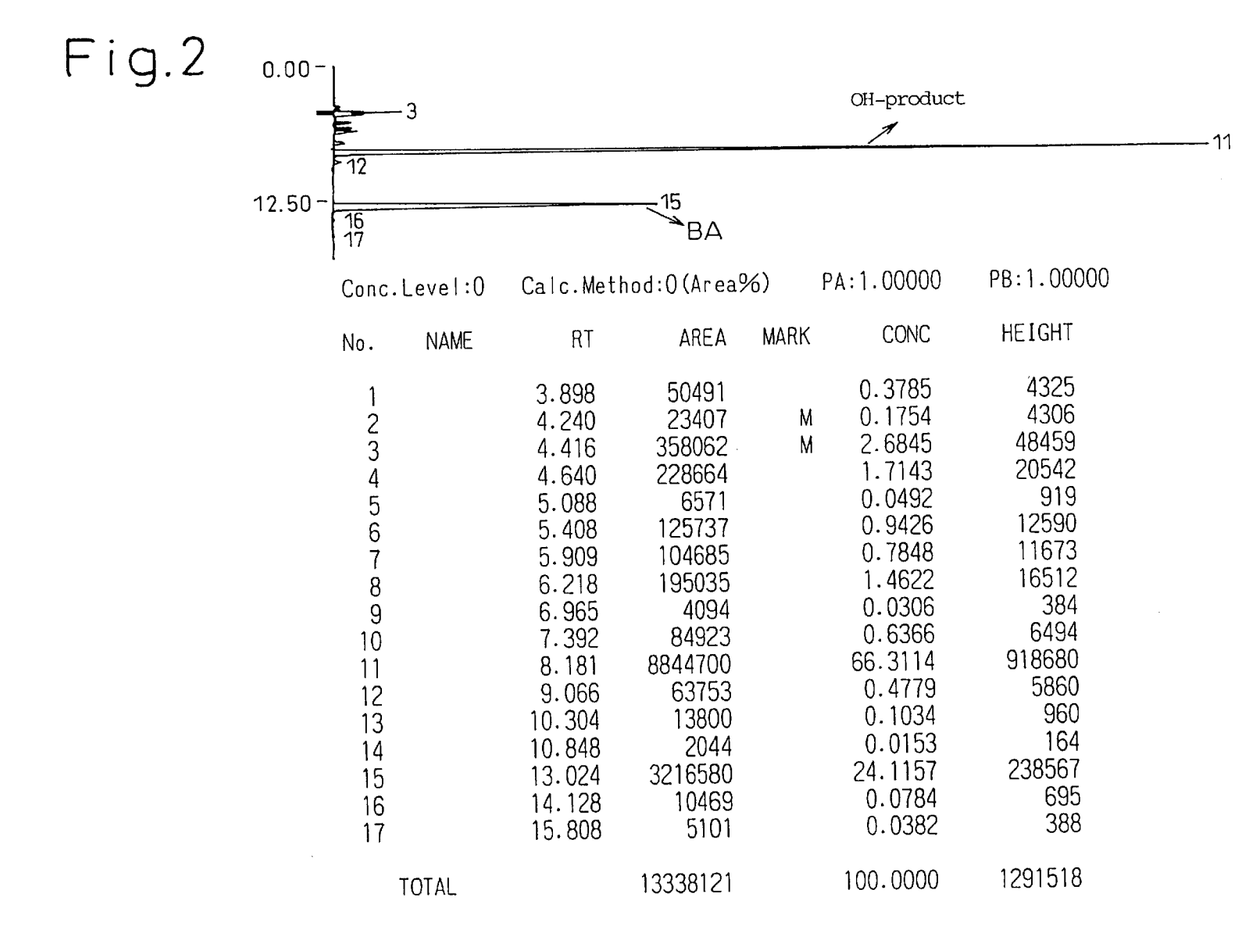
FIG. 2 is a chromatogram showing the results of the high-performance liquid chromatography (HPLC) analysis of an aqueous layer (the aqueous layer (1) as shown in FIG. 1) obtained in Example 1 by the above-mentioned liquid-separating procedure.
Figure 3:
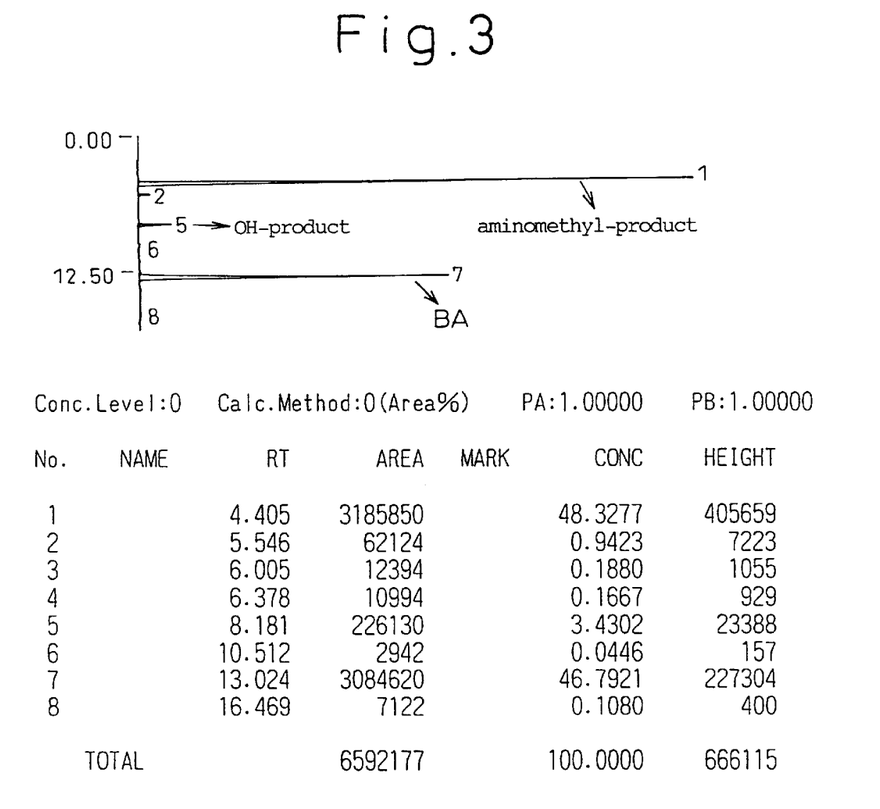
FIG. 3 is a chromatogram showing the results of the HPLC analysis of another aqueous layer (the aqueous layer (2) shown in FIG. 1) obtained in Example 1 by the above-mentioned liquid-separating procedure.
Figure 4:
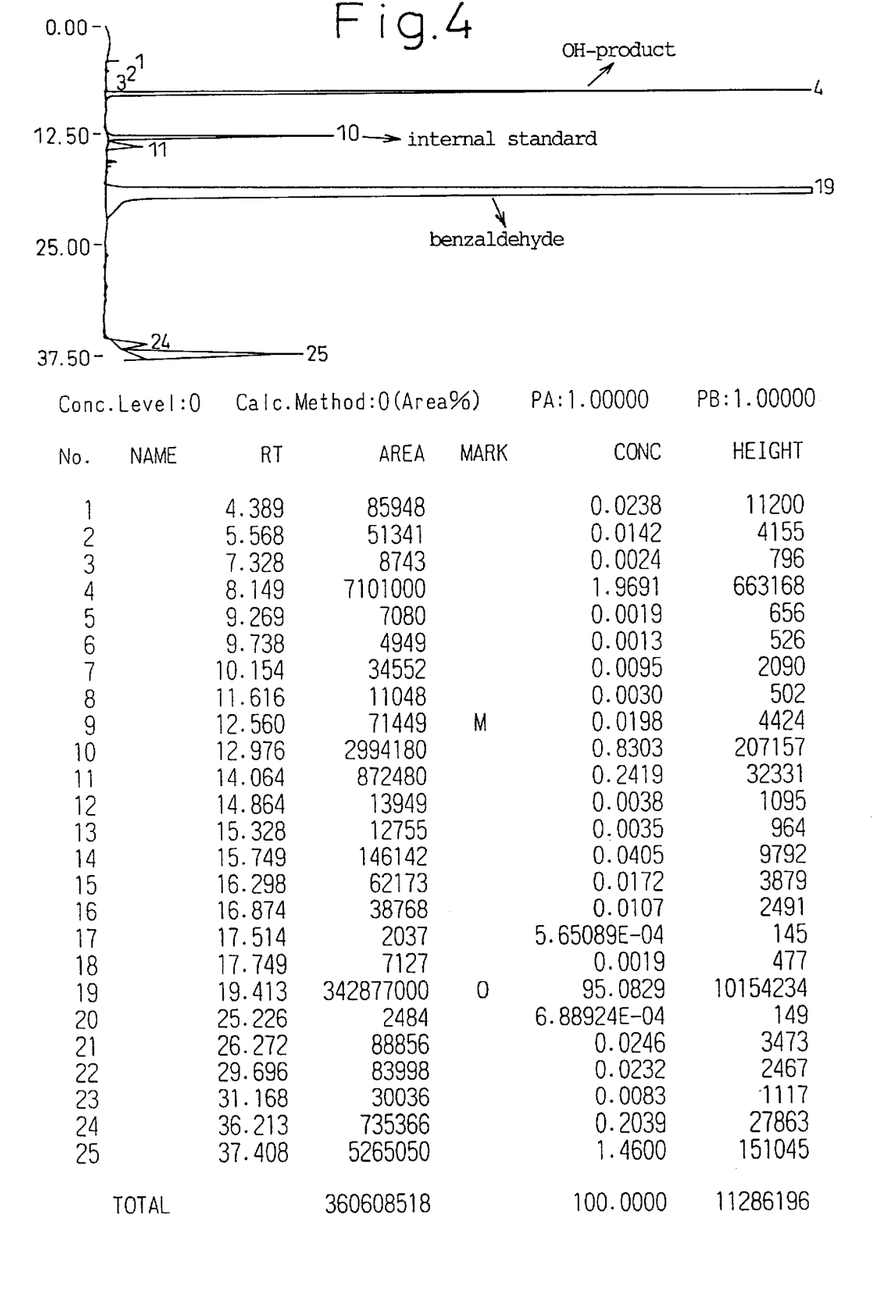
FIG. 4 is a chromatogram showing the results of the HPLC analysis of an organic layer (the organic layer shown in FIG. 1) obtained in Example 1 by the above-mentioned liquid-separating procedure.

The data obtained by the above HPLC analysis are shown in FIG. 2 (aqueous layer (1)), FIG. 3 (aqueous layer (2)), and FIG. 4 (organic layer). In these chromatograms, the "aminomethyl product" denotes 5-aminomethyl-2-chlorothiazole, the "OH-product" denotes 2-chloro-5-(hydroxymethyl)thiazole which has been obtained by the hydrolysis of the raw material, and "BA" denotes benzoic acid as an internal standard.

Example 2

16.8 g (0.1 mole) of 2-chloro-5-chloromethyl thiazole, 50 ml of water, 12.7 g (0.12 mole) of benzaldehyde and 40.9 g (0.6 mole) of a 25% aqueous ammonia solution were added into a reaction vessel, the same as that used in Example 1, and the resultant mixture was subjected to reaction under stirring at about 60° C. for 6 hours, while adding ammonia gas to the reaction mixture by bubbling so that some excess gas was emitted from the reaction mixture.

The reaction mixture was cooled to room temperature, and thereafter was extracted with 20 ml of chlorobenzene and the resultant organic layer was washed with water. Then, 13 ml of water was added to the organic layer, 10.4 g (0.1 mole) of 35% hydrochloric acid was added thereto dropwise, and the resultant mixture was stirred at 30° C. for 2 hours.

The reaction mixture was subjected to liquid separation and the resultant aqueous layer was taken out therefrom, and 20 ml of chlorobenzene was added to the aqueous layer and the mixture was stirred. The thus obtained mixture was allowed to stand and then the resultant aqueous layer was taken out therefrom and was adjusted to a pH of 13 or more by use of a 23% aqueous sodium hydroxide solution, and stirred at room temperature for 0.5 hour. The resultant aqueous solution was extracted with 20 ml of chlorobenzene three times, and the organic layer was washed with water, and was dried over anhydrous sodium sulfate (mirabilite) and was concentrated by using an evaporator to thereby obtain 14.0 g (yield 94.2%, p=95%) of crude 5-aminomethyl-2-chlorothiazole. Further, this product was distilled under reduced pressure at 73–75° C./1 mm Hg by using a vacuum pump to thereby obtain 12.8 g (yield 85.1%) of 5-aminomethyl-2-chlorothiazole having a purity of 99.5% or more.

Example 3

16.8 g (0.1 mole) of 2-chloro-5-chloromethylthiazole, 50 ml of water, 12.7 g (0.12 mole) of benzaldehyde and 40.9 g (0.6 mole) of a 25% aqueous ammonia solution were added into the reaction vessel which was the same as that used in Example 1, and the resultant mixture was subjected to reaction under stirring at about 85° C. for 5 hours. The reaction mixture was cooled to room temperature, and thereafter was extracted with chlorobenzene and the resultant organic layer was washed with water. Then, 20 ml of water was added to the organic layer, 10.4 g (0.1 mole) of 35% hydrochloric acid was added thereto dropwise, and the resultant mixture was stirred at 30° C. for 2 hours. The reaction mixture was subjected to liquid separation and the resultant aqueous layer was taken out therefrom, and chlorobenzene was added to the aqueous layer and the mixture was stirred. The mixture was allowed to stand and then the resultant aqueous layer was taken out therefrom. 10.0 g (yield 54.0%) of the desired product was obtained from this aqueous layer as 5-aminomethyl-2-chlorothiazole hydrochloride.

Example 4

16.8 g (0.1 mole) of 2-chloro-5-chloromethylthiazole, 50 ml of water, 50 ml of isopropyl alcohol, 12.7 g (0.12 mole) of benzaldehyde and 40.9 g (0.6 mole) of a 25% aqueous ammonia solution were added into a reaction vessel which was the same as that used in Example 1, and the resultant mixture was subjected to reaction under stirring at about 65° C. for 4.5 hours. The reaction mixture was cooled to room temperature, and 41.7 g (0.4 mole) of 35% hydrochloric acid was added thereto dropwise, and the resultant mixture was stirred at 30° C. for 2 hours. The reaction mixture was concentrated to about 80 ml by using a rotary evaporator, and then chlorobenzene was added thereto and the mixture was stirred. The mixture was allowed to stand and then the resultant aqueous layer was taken out therefrom. 14.9 g (yield 80.5%) of the desired product was obtained from this aqueous layer as 5-aminomethyl-2-chlorothiazole hydrochloride.

Example 5

16.8 g (0.1 mole) of 2-chloro-5-chloromethylthiazole, 12.7 g (0.12 mole) of benzaldehyde and 40.9 g (0.6 mole) of a 25% aqueous ammonia solution were placed in an autoclave and the resultant mixture was subjected to reaction at a pressure of 2 $kg/cm^2$=2×98067 Pa) at about 65° C. for 5 hours under stirring. The reaction mixture was cooled to room temperature, and 10.4 g (0.1 mole) of 35% hydrochloric acid was added thereto dropwise, and stirred at 30° C. for 2 hours. Then, chlorobenzene was added to the reaction mixture and the mixture was stirred. The mixture was allowed to stand and then the resultant aqueous layer was taken out therefrom. 15.5 g (yield 83.8%) of the desired product was obtained from this aqueous layer as 5-aminomethyl-2-chlorothiazole hydrochloride.

Example 6

80.0 kg (0.1 k mole, p=81.8) of 2-chloro-5-chloromethylthiazole, 238 liter of water, 60.6 kg (0.571 k mole) of benzaldehyde, and 194.6 kg (2.857 k mole) of a 25% aqueous ammonia solution were added into a reaction kettle (made of GL (glass lining), internal volume: about 1000 liter), and the resultant mixture was subjected to reaction under stirring for 6 hours, while supplementing ammonia gas so that the pressure at about 60° C. could be maintained at a pressurization of 20–50 cm $H_2O$ (1960–4900 Pa).

The reaction mixture was cooled to room temperature, and thereafter was extracted with 200 liter of chlorobenzene and the resultant organic layer was washed with water, and 62 liter of water was added thereto. Then, 50.0 kg (0.1 k mole) of 35% hydrochloric acid was added dropwise to the mixture and the mixture was stirred at 30° C. for 2 hours. The mixture was subjected to liquid separation and the resultant aqueous layer was taken out therefrom. Then, 200 liter of chlorobenzene was added to the aqueous layer and the resultant mixture was stirred. The mixture was allowed to stand and then the resultant aqueous layer was taken out therefrom. 57.2 kg (yield 79.4%) of the desired product was obtained from this aqueous layer as 5-aminomethyl-2-chlorothiazole hydrochloride.

The following table inclusively shows the data obtained in the above Examples 1, 2 and 5.

|  | <Example 1> | <Example 2> | <Example 5> |
|---|---|---|---|
| Equiv. of 25% aqueous ammonia solution | 6 | 6 | 6 |
| Equiv. of benzaldehyde | 1.2 | 1.2 | 1.2 |
| Water (liter/mole). | 1 | 0.5 | — |
| Reaction temperature (° C.) | 65–70 | 60 | 60 |
| Reaction time (hr) | 6 | 6 | 5 |
| Aqueous layer (1) | 7.07 | 2.19 | 0.79 |
| Aqueous layer (2) | 1.09 | 1.05 | 0.78 |
| Organic layer | 2.76 | 2 | 0.51 |
| Yield of OH-product produced (mole %) | 11.0 | 5.2 | 2.1 |
| Aminomethyl-product hydrochloride (%) | 73 | 85.4 | 83.8 |

Each of the amount of the OH-product as shown in the above Examples is the total of the respective amounts of the OH-products in the above aqueous layer (1), the aqueous layer (2) and the organic layer.

When the respective experiments were repeated, the resultant yields reproducibly showed 73–75% under the same conditions as in Example 1, and the yields reproducibly showed 82–85% under the same conditions as in Example 2.

Industrial Applicability

As described hereinbefore, the present invention can suppress the formation of by-products which can be produced at the time of the reaction of a heterocyclic halide compound with ammonia to produce an aminomethyl-heterocyclic compound, i.e., the formation of the dimer and the trimer which can be produced by a further reaction of a free aminated product to be produced and a halomethyl-thiazole as the raw material, to thereby obtain the desired aminated product in high yield with good purity.

In addition, the aromatic aldehyde used in the present invention can be regenerated at the time of the hydrolysis using mineral acid, and therefore this reagent has an advantage such that it can be recycled many times in the production process according to the present invention.

Accordingly, the present invention can provide an industrial process for producing an amino-heterocyclic derivative which is not only advantageous in view of the cost, but also is simpler and provides better yield, as compared with the conventional processes.

What is claimed is:

1. A process for producing an aminomethyl-heterocyclic derivative, wherein a heterocyclic halide compound represented by a general formula (I):

T—CH$_2$—Y    (I)

(wherein T denotes a heterocyclic group, and Y denotes a chlorine atom, bromine atom or iodine atom), is reacted with ammonia in the absence of a phase-transfer catalyst and in the presence of an aromatic aldehyde represented by a general formula (II):

A—CHO    (II)

(wherein A denotes an aromatic group), to thereby obtain a Schiff base represented by a general formula (III):

T—CH$_2$—N=CH—A    (III)

(wherein T denotes a heterocyclic group, and A denotes an aromatic group).

2. A production process according to claim 1, wherein the aminomethyl-heterocyclic derivative (III) is further hydrolyzed with mineral acid to thereby obtain a deprotected aminated product represented by a general formula (VI):

T—CH$_2$—NH$_2$    (VI)

(wherein T denotes a heterocyclic group).

3. A process for producing an aminomethyl-heterocyclic derivative, wherein a heterocyclic halide compound represented by a general formula (IV):

(IV)

(wherein X denotes a halogen atom and Y denotes a chlorine, bromine or iodine atom), is reacted with ammonia in the presence of an aromatic aldehyde represented by a general formula (V):

(V)

(wherein, Q denotes a hydrogen atom, a halogen atom or an alkyl group containing 1–5 carbon atoms, and n denotes an integer of 1 or 2), to thereby obtain a Schiff base represented by a general formula (VIII):

(VIII)

(wherein X denotes a halogen atom, Q denotes a hydrogen atom, a halogen atom or an alkyl group containing 1–5 carbon atoms, and n denotes an integer of 1 or 2).

4. A production process according to claim 3, wherein the aminomethyl-heterocyclic derivative (VIII) is further hydrolyzed with mineral acid to thereby obtain a deprotected aminated product represented by a general formula (VII):

(VII)

5. A production process according to claim 1, wherein in the reaction with ammonia in the presence of an aromatic aldehyde, ammonia is added to the reaction system by bubbling.

6. A production process according to claim 3, wherein in the reaction with ammonia in the presence of an aromatic aldehyde, ammonia is added to the reaction system by bubbling.

* * * * *